United States Patent [19]

Morton, Jr.

[11] 4,198,525

[45] Apr. 15, 1980

[54] 11-DEOXY-3,7-INTER-M-PHENYLENE-4,5,6-TRINOR-3-OXA-PGE COMPOUNDS

[75] Inventor: Douglas R. Morton, Jr., Portage, Mich.

[73] Assignee: The Upjohn Company, Kalamazoo, Mich.

[21] Appl. No.: 3,243

[22] Filed: Jan. 15, 1979

[51] Int. Cl.$^2$ ............................................. C07C 177/00
[52] U.S. Cl. ........................................ 562/471; 560/61
[58] Field of Search .......................... 560/61; 562/471

[56] References Cited

U.S. PATENT DOCUMENTS 4,100,192  7/1978  Morozowich .......................... 560/13

*Primary Examiner*—Paul J. Killos
*Attorney, Agent, or Firm*—Robert A. Armitage

[57] ABSTRACT

The present invention relates to two novel compounds, the pharmacologically acceptable salts thereof and their preparation and use as pharmacological agents. These novel compounds are 11-deoxy-3,7-inter-m-phenylene-4,5,6-trinor-3-oxa-PGE$_1$ and
11-deoxy-3,7-inter-m-phenylene-4,5,6-trinor-3-oxa-13,14-dihydro-PGE$_1$.

4 Claims, No Drawings

11-DEOXY-3,7-INTER-M-PHENYLENE-4,5,6-TRINOR-3-OXA-PGE COMPOUNDS

TECHNICAL FIELD

The present invention relates to two novel compounds, the pharmacologically acceptable salts thereof and their preparation and use as pharmacological agents. These novel compounds are
11-deoxy-3,7-inter-m-phenylene-4,5,6-trinor-3-oxa-PGE$_1$ and
11-deoxy-3,7-inter-m-phenylene-4,5,6-trinor-3-oxa-13,14-dihydro-PGE$_1$.

The preparation and use of interphenylene prostaglandins is known in the art. See, for example, U.S. Pat. Nos. 4,100,192, 4,078,083, and 3,933,898, as well as German Offenlegungsschrift No. 2,635,838.

SUMMARY OF THE INVENTION

The present invention relates to 11-deoxy-3,7-inter-m-phenylene-4,5,6-trinor-3-oxa-PGE$_1$ and its 13,14-dihydro analog. These compounds are structurally represented by formula I and formula II.

Subsequent to the invention of these compounds, they were described in U.S. Pat. No. 4,100,192 as starting materials for preparing the corresponding amides. Like the amides described in U.S. Pat. No. 4,100,192, these free acids are principally useful in the inhibition of platelet aggregation. In contrast, however, to the extremely prolonged in vivo activity of the corresponding amides, these novel free acids exhibit a surprisingly and unexpectedly short duration of activity, rendering these compounds useful for the same platelet antiaggregatory purposes, but particularly adapted for acute administration.

Additionally, the in vivo activity of the instant compounds, being of a relatively short duration, renders these compounds surprisingly and unexpectedly useful when employed in extracorporeal circulation and in blood or plasma storage. Thus, the compounds of the instant invention are peculiarly and particularly adapted to numerous pharmacological purposes for which the more prolonged, orally acting amides are ill-suited.

Accordingly, the present invention provides methods of accomplishing surgical procedures and other procedures involving extracorporeal circulations (e.g., hemodialysis, heart-lung oxygenation), by parenteral use of these novel substances.

The novel 11-deoxy-3,7-inter-m-phenylene-4,5,6-trinor-3-oxa-PGE$_1$ compounds of the present invention are substantially equally potent to PGE$_1$ as in vitro platelet aggregation inhibitors. Accordingly, the novel compounds herein are useful as blood additives in extracorporeal circulations at concentrations of 1–100 ng/ml in the manner which PGE$_1$ is used for these purposes. When given by IV injection to a patient, appropriate dosages are those in the range 1–100 μg/kg, with periodic repetition (e.g. at 2–4 hr intervals).

The present invention also relates to pharmacologically acceptable salts of the novel prostaglandin analogs described above. The salts contemplated for use in accordance with the present invention are those conventionally employed with prostaglandins (e.g., amine salts), and facilitate the use of these compounds for parenteral administration. See U.S. Pat. No. 4,016,184 for a more detailed description of such salts.

A. The novel compounds of the instant invention are prepared in accordance with the following examples:

EXAMPLE 1

11-deoxy-3,7-inter-m-phenylene-4,5,6-trinor-3-oxa-PGE$_1$ 3,7-inter-m-phenylene-4,5,6-trinor-3-oxa-PGE$_1$, bis(-tetrahydropyranyl ether), 2.17 g of an oil, is dissolved in 5 ml of tetrahydrofuran, 30 ml glacial acetic acid, and 15 ml of water. The resulting mixture is then stirred at 40° C. for 2.5 hr and the reaction mixture diluted with 300 ml water. Lyophilization yields a crude semi-solid mixture (2.44 g) containing 3,7-inter-m-phenylene-4,5,6-trinor-3-oxa-PGA$_1$. Chromatography on 200 g of acid-washed silica gel packed in 50% ethyl acetate in n-hexane, eluting with 50–100% ethyl acetate in n-hexane, yields 0.02 g of partially pure product in fractions 22–27 (40 ml fractions collected). Rechromatographing on acid-washed silica gel, eluting with 30–50% ethyl acetate in Skellysolve B, yields pure 3,7-inter-m-phenylene-4,5,6-trinor-3-oxa-PGA$_1$ as an oil. NMR absorptions are observed at 0.88, 0.6–1.9, 2.15–3.47, 3.97, 4.63, 5.28, 6.12–6.33, 7.38–7.60, and 6.62–7.4 ppm. The mass spectrum of the trimethylsilyl derivative exhibits a high resolution peak at 516.2743 and other peaks at 501, 445, 426, 235, 199, and 173. Silica gel TLC Rf is 0.31 in the A-IX solvent system. The A-IX solvent system is prepared from ethyl acetate-acetic acid-2,2,4-trimethylpentane-water (90:20:50:100), as modified from M. Hamberg and B. Samuelsson, J. Biol. Chem. 241:275 (1966).

B. The reaction product of Part A (1 g), 5 ml of pyridine, and 2 ml of acetic anhydride are stirred at 25° C. for 12 hr, diluted with 25 ml of saturated aqueous sodium bicarbonate, and stirred for at 25° C. for 2 hr. The resulting mixture is then diluted with brine, adjusted to pH3 by addition of 1 M aqueous potassium bisulfate, and extracted with ethyl acetate. The organic extracts are then washed with brine, dried over sodium sulfate, and concentrated under reduced pressure to yield about 1.13 g of 3,7-inter-m-phenylene-4,5,6-trinor-3-oxa-PGA$_1$, 15-acetate as an oil. Silica gel TLC Rf is 0.45 in the A-IX solvent system.

C. The reaction product of Part B is then dissolved in 10 ml of methanol and treated with 0.41 g of sodium borohydride and 5 ml of water. The resulting mixture is then stirred at 25° C. for 30 min, diluted with brine, acidified to pH3 by addition of 1 M aqueous potassium bisulfate, and extracted with ethyl acetate. The organic extracts are then washed twice with brine, dried over sodium sulfate, and concentrated under reduced pressure to yield 0.93 g of 3,7-inter-m-phenylene-4,5,6-trinor-3-oxa-11-deoxy-PGF$_1$, 15 acetate as an oil. Silica gel TLC Rf is 0.41 in the A-IX solvent system.

D. The reaction product of Part C is then dissolved in acetone and the resulting solution cooled to −25° C. and treated with 1.1 ml of 2.67 M Jones reagent. The resulting mixture is then stirred at −15° to −20° C. for 2 min. Thereafter isopropanol (2 ml) was added and the resulting mixture is stirred at −15° to −20° C. for 15 min. After elution with brine, and extraction with ethyl acetate, the organic extracts are then washed with brine, dried over sodium sulfate, and concentrated under reduced pressure to yield 0.89 g of an oil. This material is then dissolved in 25 ml of acetonitrile and treated with 2 ml of methyl iodide and 5 ml of diisopropylethylamine. The resulting mixture is then stirred at 25° C. for 7 hr, diluted with brine, and extracted with ethyl acetate. The organic extracts are then washed successively with 1 N aqueous hydrochloric acid, saturated aqueous sodium bicarbonate, and brine; dried over sodium sulfate; and concentrated under reduced pressure to yield 0.83 g of 3,7-inter-m-phenylene-4,5,6-trinor-3-oxa-11-deoxy-PGE$_1$, methyl ester, 15-acetate as an oil. Chromatographing on 44 g of silica gel packed in methylene chloride and eluting with 1% acetone in methylene chloride yields 0.41 g of pure 3,7-inter-m-phenylene-4,5,6-trinor-3-oxa-11-deoxy-PGE$_1$, methyl ester, 15-acetate as an oil. NMR absorptions are observed at 0.88, 0.8–2.7, 2.02, 2.88, 3.78, 4.59, 5.20, 5.52, and 6.55–7.38$\delta$. Characteristic infrared absorptions are observed at 1765, 1745, and 1240 cm$^{-1}$.

The mass spectrum exhibits a high resolution peak at 430.2350 and other peaks at 388, 370, 339, 261, 251, 191, and 179. Silica gel TLC Rf is 0.22 in acetone and methylene chloride (2:98).

E. The reaction product of Part D is dissolved in 10 ml of methanol and 4 ml of water and treated with 0.53 g of potassium carbonate. The resulting mixture is then stirred at ambient temperature overnight, diluted with brine, acidified to pH3 with 1 M aqueous potassium bisulfate, and extracted with ethyl acetate. The combined organic extracts are then washed with brine, dried over sodium sulfate, and concentrated under reduced pressure to yield 0.39 g of crude title product (3,7-inter-m-phenylene-4,5,6-trinor-3-oxa-11-deoxy-PGE$_1$). Chromatography on acid-washed silica gel, packed with 25% ethyl acetate in Skellysolve B and eluted with 25–40% ethyl acetate in Skellysolve B yields 0.32 g of pure title product. NMR absorptions are observed at 0.88, 0.8–2.8, 2.88, 4.03, 4.60, 5.49, 6.4–7.4, and 6.78$\delta$. Infrared absorptions are observed at 3460, 2620, 2560, 1740, 1605, 1590, 1490, 1220, 1160, 1085, 975 cm$^{-1}$. The mass spectrum for the bis-trimethylsilyl derivative exhibits a high resolution peak at 518.2869 and other peaks at 503, 447, 428, 419, 413, 404, 391, 357, 332, 331, 313, 237, and 199. Silica gel TLC Rf is 0.36 in the A-IX solvent system.

EXAMPLE 2

3,7-inter-m-phenylene-4,5,6-trinor-3-oxa-11-deoxy-13,14-dihydro-PGE$_1$.

3,7-Inter-m-phenylene-4,5,6-trinor-3-oxa-PGA$_1$ (0.10 g), 10 ml of ethyl acetate, and 0.10 g of 5% palladium-on-carbon catalyst are combined at atmospheric pressure and hydrogenated (hydrogen gas) at atmospheric temperature for 30 min. When uptake of hydrogen ceases, the resulting mixture is then filtered through celite and concentrated under reduced pressure to yield 0.10 g of crude title product. Chromatographing on 10 g of acid-washed silica gel, packed with 10% ethyl acetate in Skellysolve B and eluting with 10–40% ethyl acetate in Skellysolve B yeilds 69 mg of pure title product as an oil. NMR absorptions are observed at 0.88, 0.8–3.23, 3.55, 4.63, 6.05, and 6.63–7.47$\delta$. Infrared absorptions are observed at 3450, 2620, 2550, 1735, 1605, 1585, 1490, 1230, 1160, and 1085 cm$^{-1}$. The mass spectrum for the bis-trimethylsilyl derivative exhibits a high resolution peak at 520.3026 and other peaks at 505, 449, 430, 415, 391, 332, 319, 241, 237, 193, and 173 cm$^{-1}$. Silica gel TLC Rf is 0.35 in the A-IX solvent system.

FORMULAS

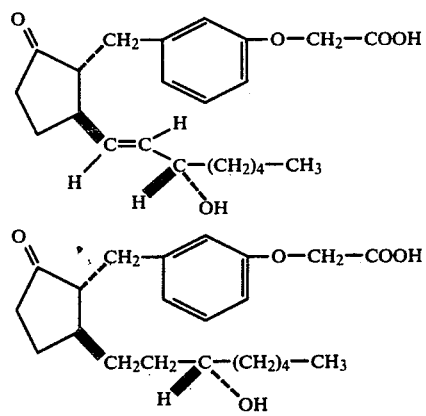

I claim:
1. 3,7-Inter-m-phenylene-4,5,6-trinor-3-oxa-11-deoxy-PGE$_1$.
2. Pharmacologically acceptable salts of 3,7-inter-m-phenylene-4,5,6-trinor-3-oxa-11-deoxy-PGE$_1$.
3. 3,7-Inter-m-phenylene-4,5,6-trinor-3-oxa-11-deoxy-13,14-dihydro-PGE$_1$.
4. Pharmacologically acceptable salts of 3,7-inter-m-phenylene-4,5,6-trinor-3-oxa-11-deoxy-13,14-dihydro-PGE$_1$.

* * * * *

UNITED STATES PATENT OFFICE
CERTIFICATE OF CORRECTION

Patent No. 4,198,525               Dated 15 April 1980

Inventor(s) Douglas R. Morton, Jr.

It is certified that error appears in the above-identified patent and that said Letters Patent are hereby corrected as shown below:

Column 2, line 1, "A. The novel" should read -- The novel --; line 8, "3,7-inter-m-phenylene-" should read -- A. 3,7-inter-m-phenylene- --; line 18, "0.02 g" should read -- 0.20 g --;
Column 4, line 8, "yeilds" should read -- yields --.

Signed and Sealed this

Tenth Day of March 1981

[SEAL]

Attest:

RENE D. TEGTMEYER

Attesting Officer      Acting Commissioner of Patents and Trademark